US012310550B2

(12) United States Patent
Miyayashiki

(10) Patent No.: US 12,310,550 B2
(45) Date of Patent: May 27, 2025

(54) ENDOSCOPE CALIBRATION SYSTEM, ENDOSCOPE DEVICE, ENDOSCOPE DEVICE CALIBRATION METHOD, AND COMPUTER-READABLE STORAGE MEDIUM

(71) Applicant: Evident Corporation, Nagano (JP)

(72) Inventor: Hidehiro Miyayashiki, Akishima (JP)

(73) Assignee: Evident Corporation, Nagano (JP)

( * ) Notice: Subject to any disclaimer, the term of this patent is extended or adjusted under 35 U.S.C. 154(b) by 580 days.

(21) Appl. No.: 17/569,192

(22) Filed: Jan. 5, 2022

(65) Prior Publication Data
US 2022/0240756 A1    Aug. 4, 2022

(30) Foreign Application Priority Data

Jan. 29, 2021    (JP) .................................. 2021-012689

(51) Int. Cl.
*A61B 1/00*    (2006.01)

(52) U.S. Cl.
CPC ...... *A61B 1/00057* (2013.01); *A61B 1/00009* (2013.01)

(58) Field of Classification Search
CPC ............ A61B 1/00057; A61B 1/00059; A61B 1/00101; A61B 1/00105; A61B 1/0011; A61B 1/00137
See application file for complete search history.

(56) References Cited

U.S. PATENT DOCUMENTS

| | | | |
|---|---|---|---|
| 8,758,223 B1 * | 6/2014 | Bodor ................ | A61B 1/00057 356/73.1 |
| 2004/0143162 A1 * | 7/2004 | Krattiger ............ | A61B 1/00101 600/129 |

(Continued)

FOREIGN PATENT DOCUMENTS

| JP | 2007-171941 A | 7/2007 |
|---|---|---|
| JP | 2012-147871 A | 8/2012 |
| JP | 2016-195684 A | 11/2016 |

OTHER PUBLICATIONS

Japanese Notice of Allowance dated Feb. 20, 2024 received in 2021-012689.

*Primary Examiner* — Aaron B Fairchild
*Assistant Examiner* — Stephen Floyd London
(74) *Attorney, Agent, or Firm* — Scully, Scott, Murphy & Presser, P.C.

(57) ABSTRACT

An endoscopic calibration system that calibrates an endoscope, includes: an imaging part that acquires an image by an optical system in which an optical adapter and a scope of the endoscope are combined; a parameter measurement part that measures a first parameter indicating optical characteristics of an optical system in which a first scope and a first optical adapter are combined, a second parameter indicating optical characteristics of an optical system in which the first scope and a second optical adapter are combined, and a third parameter indicating optical characteristics of an optical system in which the second scope and the first optical adapter are combined; and a parameter estimation part that estimates a fourth parameter indicating optical characteristics of an optical system in which the second scope and the second optical adapter are combined using the first parameter, the second parameter, and the third parameter.

14 Claims, 10 Drawing Sheets

(56) References Cited

U.S. PATENT DOCUMENTS

| | | | |
|---|---|---|---|
| 2007/0139953 A1* | 6/2007 | Krattiger | A61B 1/042 362/574 |
| 2009/0284588 A1* | 11/2009 | Matsui | A61B 1/00101 348/E7.085 |
| 2010/0004507 A1* | 1/2010 | Nakano | A61B 1/00126 600/112 |
| 2014/0246563 A1* | 9/2014 | McCaffrey | A61B 1/00057 250/208.1 |
| 2016/0295085 A1 | 10/2016 | Aoyama | |
| 2018/0325354 A1* | 11/2018 | Saito | G06T 7/35 |
| 2019/0282066 A1* | 9/2019 | Culman | G02B 23/2423 |
| 2019/0298154 A1* | 10/2019 | Mach | G02B 23/2476 |
| 2021/0265052 A1* | 8/2021 | Morishima | A61B 1/00103 |

* cited by examiner

FIG. 6

| STEP | OPTICAL ADAPTER 2 | SCOPE 16 | PARAMETER TO BE ACQUIRED |
|---|---|---|---|
| STEP S1 | 2S<br>REFERENCE OPTICAL ADAPTER | 16S<br>REFERENCE SCOPE | PARAMETER P1 |
| STEP S2 | 2U<br>USER OPTICAL ADAPTER | 16S<br>REFERENCE SCOPE | PARAMETER P2 |
| STEP S3 | 2S<br>REFERENCE OPTICAL ADAPTER | 16U<br>USER SCOPE | PARAMETER P3 |

FIG. 7

| STORING DESTINATION | PARAMETER TO BE STORED |
|---|---|
| STORAGE MEDIUM M | PARAMETER P1 PARAMETER P2 |
| STORAGE 19 OF USER SCOPE 16U | PARAMETER P1 PARAMETER P3 |

FIG. 8

| STEP | OPTICAL ADAPTER 2 | SCOPE 16 | COMBINED PARAMETERS | PARAMETER TO BE CALCULATED |
|---|---|---|---|---|
| STEP C1 | 2U<br>USER OPTICAL ADAPTER | 16U<br>USER SCOPE | PARAMETER P1<br>PARAMETER P2<br>PARAMETER P3 | PARAMETER P4 |

FIG. 9

| STEP | OPTICAL ADAPTER 2 | SCOPE 16 | PARAMETER TO BE ACQUIRED |
|---|---|---|---|
| STEP S1 | 2S<br>REFERENCE OPTICAL ADAPTER | 16S<br>REFERENCE SCOPE | PARAMETER P1 |
| STEP S2 | 2U<br>USER OPTICAL ADAPTER | 16S<br>REFERENCE SCOPE | PARAMETER P2 |
| STEP S3 | 2S<br>REFERENCE OPTICAL ADAPTER | 16U<br>USER SCOPE | PARAMETER P3 |
| STEP S4 | 2U<br>USER OPTICAL ADAPTER | 16U<br>USER SCOPE | PARAMETER P4 |

FIG. 10

| STORING DESTINATION | PARAMETER TO BE STORED |
|---|---|
| STORAGE MEDIUM M | PARAMETER P1 PARAMETER P2 |
| STORAGE 19 OF USER SCOPE 16U | PARAMETER P1 PARAMETER P3 PARAMETER P4 |

FIG. 11

| STEP | OPTICAL ADAPTE 2 | SCOPE 16 | PARAMETER TO BE ACQUIRED |
|---|---|---|---|
| STEP R1 | 2T<br>SECOND REFERENCE OPTICAL ADAPTER | 16S<br>REFERENCE SCOPE | UPDATED PARAMETER P1 |
| STEP R2 | 2T<br>SECOND REFERENCE OPTICAL ADAPTER | 16U<br>USER SCOPE | UPDATED PARAMETER P3 |

ENDOSCOPE CALIBRATION SYSTEM, ENDOSCOPE DEVICE, ENDOSCOPE DEVICE CALIBRATION METHOD, AND COMPUTER-READABLE STORAGE MEDIUM

BACKGROUND

Technical Field

The present invention relates to an endoscope calibration system, an endoscope device, a method of calibrating an endoscope device, and a computer-readable storage medium storing an endoscope calibration program.

Priority is claimed on Japanese Patent Application No. 2021-012689, filed Jan. 29, 2021, the content of which is incorporated herein by reference.

Background Art

In an endoscope device in which a part of an optical system can be changed by an optical adapter, optical distortion inherent may occur in the optical system in which a scope of the endoscope and the optical adapter are combined. In the conventional endoscopic device described in Japanese Unexamined Patent Publication No. 2007-171941 (hereinafter referred to as Patent Document 1) and the like, a method of measuring in advance parameters indicating optical characteristics of a scope and an optical adapter that can be measured in advance, and correcting an optical distortion unique to an optical system in which the scope and the optical adapter are combined by combining pre-measured parameters has been proposed However, in the conventional endoscope device described in Patent Document 1 and the like, it is necessary to respectively measure the parameters of the scope with which the optical adapter is not attached and the parameters of the scope with which the optical adapter is attached, and separate calibration means and equipment were required. Further, in the conventional endoscopic device described in Patent Document 1 and the like, it is necessary to calculate the difference parameter of the scope in advance in the method of correcting the optical characteristics including the optical distortion from the various measured parameters, and the parameters combining the optical adapter and the scope cannot be calculated directly, which makes the work and calculation complicated.

SUMMARY

The present invention provides an endoscope calibration system, an endoscope device, a method of calibrating an endoscope device, and a computer-readable storage medium storing an endoscope calibration program by which the inherent optical characteristics in an optical system in which an endoscope scope and an optical adapter are combined can be corrected by a simpler method.

An endoscopic calibration system that calibrates an endoscope in which a part of an optical system can be changed by an optical adapter, includes: an imaging part configured to acquire an image by an optical system in which the optical adapter and a scope of the endoscope are combined; a parameter measurement part configured to measure a first parameter indicating optical characteristics of an optical system in which a first scope and a first optical adapter are combined, a second parameter indicating optical characteristics of an optical system in which the first scope and a second optical adapter are combined, and a third parameter indicating optical characteristics of an optical system in which the second scope and the first optical adapter are combined; and a parameter estimation part configured to estimate a fourth parameter indicating optical characteristics of an optical system in which the second scope and the second optical adapter are combined using the first parameter, the second parameter, and the third parameter.

An endoscope device includes: an endoscope in which a part of an optical system can be changed by an optical adapter; and a control device configured to control the endoscope. The control device is configured to receive, from an external device, a first parameter indicating optical characteristics of an optical system in which a first scope and a first optical adapter are combined, a second parameter indicating optical characteristics of an optical system in which the first scope and a second optical adapter are combined, and a third parameter indicating optical characteristics of an optical system in which the second scope and the first optical adapter are combined, and to estimate a fourth parameter indicating optical characteristics of an optical system in which the second scope and the second optical adapter are combined using the first parameter, the second parameter, and the third parameter.

A method of calibrating an endoscope device in which a part of an optical system can be changed by an optical adapter, includes: measuring a first parameter indicating optical characteristics of an optical system in which a first scope and a first optical adapter are combined; measuring a second parameter indicating optical characteristics of an optical system in which the first scope and a second optical adapter are combined; measuring a third parameter indicating optical characteristics of an optical system in which a second scope and the first optical adapter are combined; and estimating a fourth parameter indicating optical characteristics of an optical system in which the second scope and the second optical adapter are combined using the first parameter, the second parameter, and the third parameter.

A computer-readable storage medium storing an endoscope calibration program makes a computer, which is equipped with an endoscope device in which a part of an optical system can be changed by an optical adapter, execute: measuring a first parameter indicating optical characteristics of an optical system in which a first scope and a first optical adapter are combined; measuring a second parameter indicating optical characteristics of an optical system in which the first scope and a second optical adapter are combined; measuring a third parameter indicating optical characteristics of an optical system in which a second scope and the first optical adapter are combined; and estimating a fourth parameter indicating optical characteristics of an optical system in which the second scope and the second optical adapter are combined using the first parameter, the second parameter, and the third parameter.

According to the endoscope calibration system, the endoscope device, the method of calibrating the endoscope device, and the computer-readable storage medium storing the endoscope calibration program of the present invention, the inherent optical characteristics of an optical system in which the scope of the endoscope and the optical adapter are combined can be corrected by a simpler method.

BRIEF DESCRIPTION OF THE DRAWINGS

FIG. 6 is a diagram illustrating parameters measured by an optical characteristic measurement device of the endoscope calibration system.

FIG. 7 is a diagram showing a storage destination of measured parameters.

FIG. 8 is a diagram showing parameters calculated by a calibration device of the endoscope calibration system.

FIG. 9 is a diagram showing parameters measured by an optical characteristic measurement device of the endoscope calibration system according to a second embodiment.

FIG. 10 is a diagram showing a storage destination of measured parameters in the endoscope calibration system.

FIG. 11 is a diagram showing parameters measured by an optical characteristic measurement device of the endoscope calibration system according to a third embodiment.

DETAILED DESCRIPTION OF THE PREFERRED EMBODIMENTS N

First Embodiment

The endoscope calibration system 200 according to the first embodiment of the present invention will be described with reference to FIGS. 1 to 8.

[Endoscope Device 100]

Figure 1:
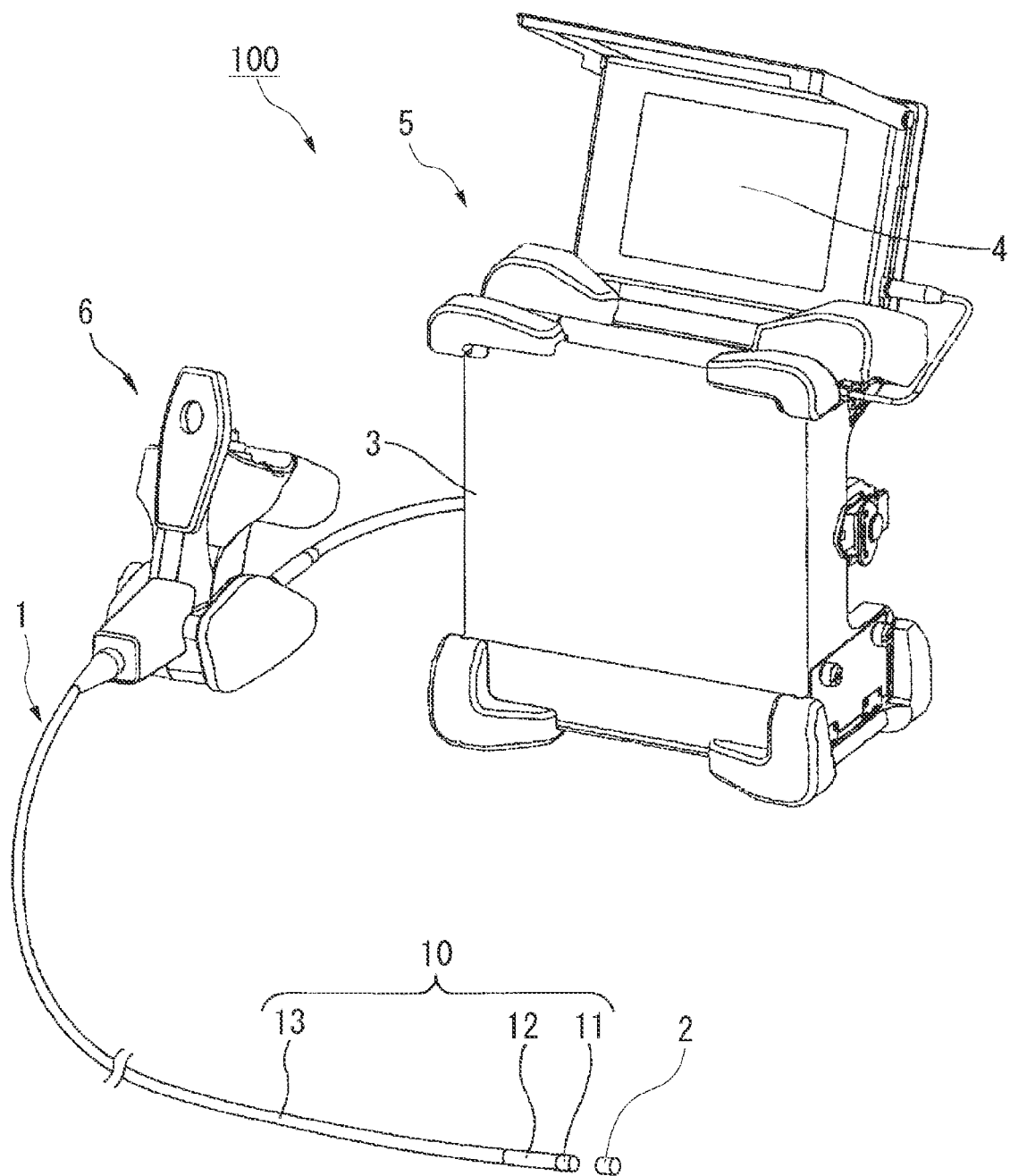
FIG. 1 is a perspective view of an endoscope device of the endoscope calibration system according to a first embodiment.

FIG. 1 is a perspective view of the endoscope device 100.

The endoscope device 100 is an industrial endoscope device, and includes an endoscope 1, a control device 3, a display part 4, a device main body 5, and an operation part 6. The display part 4 displays an image of the subject captured by the endoscope 1, an operation menu, a measurement image, and the like. The device main body 5 is a housing for storing the control device 3. The operation part 6 is an input device for inputting operations necessary for controlling the endoscope 1.

The display part 4 is provided integrally with the device main body 5. The display of the display part 4 is arranged on the surface of the device main body 5. The display part 4 is a liquid crystal display, an organic EL display, a CRT (Cathode Ray Tube) display, or the like. The display of the display part 4 may be a touch panel. The display part 4 may be provided on an external terminal capable of communicating with the endoscope device 100. The external terminal is, for example, a computer, a mobile phone, a tablet, a smartphone, or the like.

The operation part 6 has a curved operation part and a button operation part. A joystick, a lever, or the like is arranged in the curved operation part. The user can bend the curved part 12 by operating the joystick or the lever. Multiple switches are arranged in the button operation part. The user can control the imaging operation and the measurement operation by the endoscope device 100 by operating the switch. These operations may be performed from an external terminal capable of communicating with the endoscope device 100. The external terminal is, for example, a computer, a mobile phone, a tablet, a smartphone, or the like.

[Endoscope 1]

The endoscope 1 includes an elongated insertion part 10 and an optical adapter 2 that can be attached to and detached from the insertion part 10. The endoscope 1 can change a part of the optical system by exchanging the optical adapter 2.

The insertion part 10 is inserted inside the subject to be observed or measured. The insertion part 10 has a rigid distal end part 11, a plurality of curved parts 12 that can be curved in different directions, and a flexible tube part 13 that has flexibility. The distal end part 11, the curved part 12, and the flexible pipe part 13 are connected in order from the distal end side. The flexible pipe part 13 is connected to the operation part 6. The insertion part 10 forms an optical system by attaching an optical adapter that can be attached to and detached from the insertion part 10 to the distal end part 11, and can be observed and measured.

Figure 2:
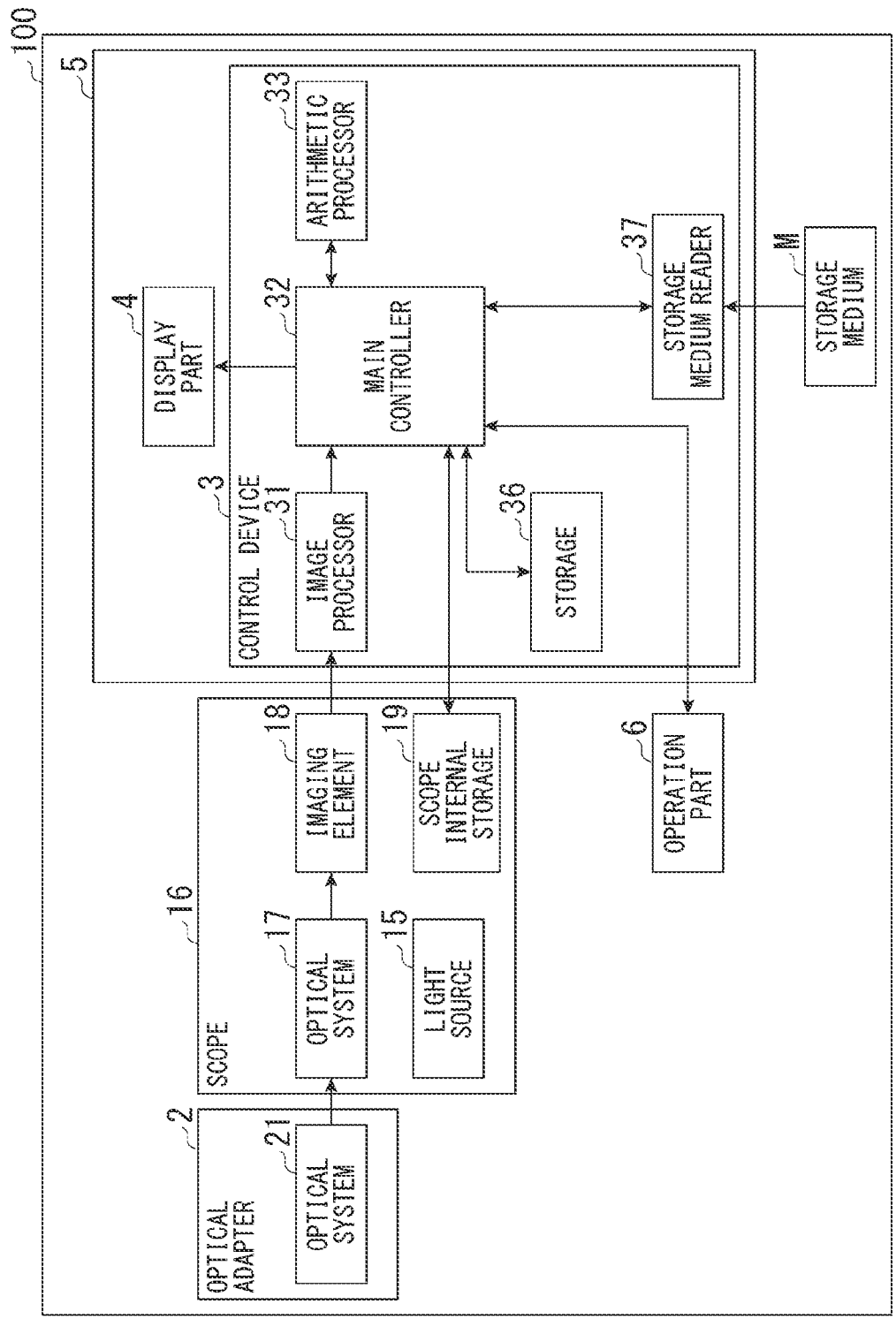
FIG. 2 is a functional block diagram showing an internal configuration of the endoscope device.

FIG. 2 is a functional block diagram showing the internal configuration of the endoscope device 100.

The distal end part 11 has a scope 16. The scope 16 includes a light source 15, an optical system 17, an imaging element 18, and a scope internal storage 19. An optical adapter 2 for forming a subject image can be attached to and detached from the distal end part 11.

The scope 16 may be equipped with a replaceable scope unit. The user may attach a scope unit corresponding to the purpose of use, such as an observation scope unit, a measurement scope unit, or a scope unit having a different length or diameter. In addition, the user may replace the old scope unit with a new (different individual) scope unit of the same type.

The light source 15 is a light source that emits light that irradiates the subject. The light source 15 emits light at a light amount and timing according to the drive signal output from the control device 3. The light source 15 may include, for example, a white LED (Light Emitting Diode) light source, or a plurality of LEDs that emit light having a plurality of different wavelengths, such as R (red), G (green), and B (blue).

The imaging element 18 photoelectrically converts the image of the subject imaged via the optical system 17 to generate an imaging signal. The imaging element 18 is, for example, a CCD image sensor, a CMOS image sensor, or the like.

The scope internal storage 19 is a non-volatile recording medium that records information different for each individual scope 16 such as parameters related to the scope 16 and ID information (individual identification number such as a serial number). The scope internal storage 19 is composed of, for example, a writable non-volatile memory such as a ROM or a flash memory.

The optical adapter 2 is an adapter that can be attached to and detached from the insertion part 10 of the distal end part 11, and is, for example, a stereo measurement optical adapter. The optical adapter 2 has an optical system 21. The optical system 21 of the optical adapter 2 is combined with the optical system 17 of the scope 16 to form the optical system of the endoscope 1. The optical system of the endoscope 1 causes the light of the subject image to enter the imaging element 18.

Figure 3:
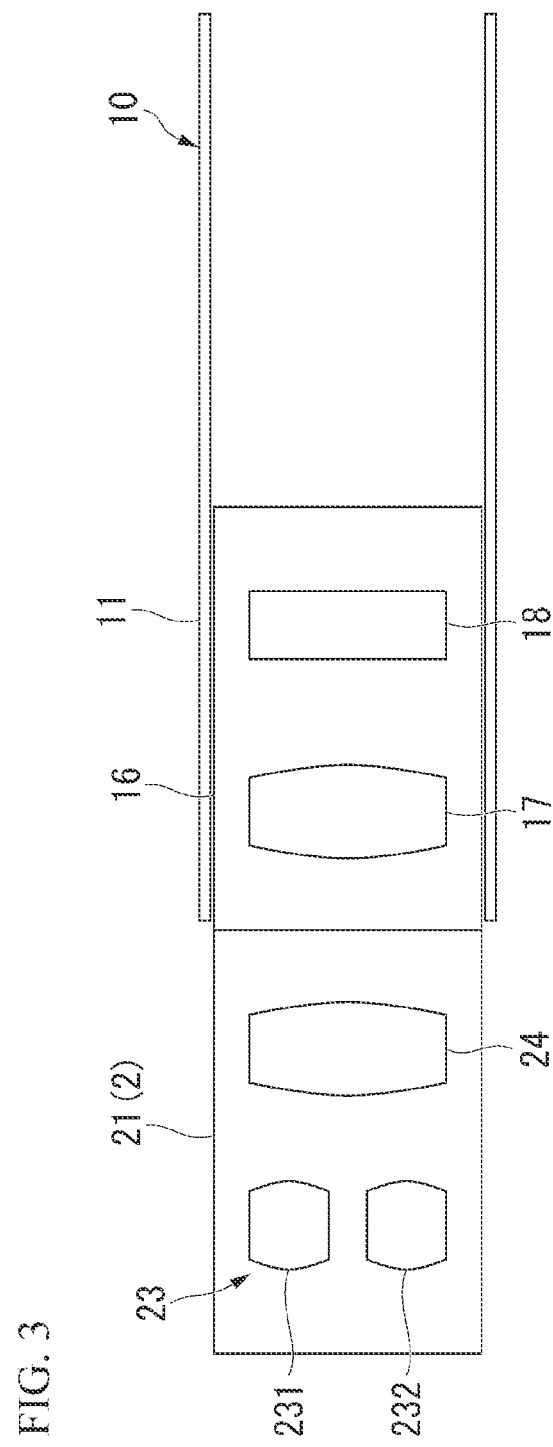
FIG. 3 is a schematic view showing an optical adapter and a scope of the endoscope device.

FIG. 3 is a schematic view showing the optical adapter 2 and the scope 16.

The optical system 21 of the optical adapter 2 has two objective lenses 23 (first objective lens 231 and second objective lens 232) and a relay optical system 24.

Each of the two objective lenses 23 (first objective lens 231 and second objective lens 232) is an optical lens that emits incident light, that is, reflected light from the subject irradiated with the light emitted by the light source 15 toward the imaging element 18 and forms a subject image on the imaging element 18. Each of the first objective lens 231 and the second objective lens 232 is an optical lens that forms an image of reflected light from a subject in the same (common) imaging region. Each of the first objective lens 231 and the second objective lens 232 forms an image of the reflected light from the subject over the entire imaging region of the imaging element 18. One of the first objective lens 231 and the second objective lens 232 is an optical lens corresponding to the right eye, and the other is an optical lens corresponding to the left eye. Therefore, parallax appears in the subject image formed by each of the first objective lens 231 and the second objective lens 232 on the imaging element 18. As a result, the endoscope device 100 can generate a three-dimensional image of the subject and perform stereo measurement.

The optical adapter 2 is not limited to the stereo measurement optical adapter, and may have various optical systems such as binocular, monocular, direct vision, and lateral vision as long as it can measure. Further, the measurement method using the optical adapter 2 is not limited to the stereo measurement described above, and may be phase measurement including, for example, a phase shift method.

The relay optical system 24 relays light rays from the optical adapter 2 side to the scope 16 side, and parallelizes the light rays from the stereo optical system. The relay optical system 24 may include a movable light-shielding member or the like. The light-shielding member or the like includes a mechanical mechanism (for example, an actuator) that switches the light incident on the imaging element 18 from the two objective lenses 23 (first objective lens 231 and second objective lens 232), for example, by moving a light-shielding member or the like.

As shown in FIG. 2, the control device 3 includes an image processor 31, a main controller 32, an arithmetic processor 33, a storage 36, and a storage medium reader 37.

The image processor 31 drives the imaging element 18 and acquires an imaging signal from the imaging element 18. The image processor 31 converts the imaging signal into a video signal such as an NTSC signal. The generated video image is transferred to the display part 4. The imaging element 18, the image processor 31, and the main controller 32 are examples of the "imaging part".

As shown in FIG. 10, the control device 3, particularly the main controller 32, is a program-executable processing device (computer) having one or more processors and a memory or the like capable of reading a program. The main controller 32 calibrates the endoscope device 100 by executing an endoscope calibration program. Each of the one or more processors is hardware including, for example, a CPU (Central Processor), a GPU (Graphics Processor), a DSP (Digital Signal Processor), and the like, and performs programmed processing by executing a program (not shown) stored in one or more memories or the like. Further, the one or more processors may include an ASIC (Application Specific Integrated Circuit), an FPGA (Field-Programmable Gate Array), and the like.

The arithmetic processor 33 performs a part or all of the arithmetic processing in the measurement and calibration performed when the endoscope device 100 is calibrated. The arithmetic processor 33 is composed of, for example, a dedicated arithmetic circuit. The dedicated arithmetic circuit is a processor (CPU, GPU, DSP, etc.) separate from the processor of the main controller 32, a logic circuit mounted on an ASIC or FPGA, or a combination thereof. That is, the control device 3 is composed of the above-mentioned one or more processors and a dedicated arithmetic circuit.

At least a part of the processing of the image processor 31 and the arithmetic processor 33 may be performed by the main controller 32.

The storage 36 is a non-volatile computer-readable recording medium that stores the above-mentioned program and necessary data. The storage 36 is, for example, one or more arbitrary semiconductor memories, and is composed of a writable non-volatile memory such as a flexible disk, a magneto-optical disk, a ROM, or a flash memory, a portable medium such as a CD-ROM, or a storage device such as a hard disk built in a computer system.

The storage medium reader 37 can attach and detach a removable recording medium M such as a USB memory, an external hard disk, or a memory card, and can read the recorded data from the mounted recording medium M. The read data is transferred to the main controller 32. The data recorded on the recording medium M is, for example, parameters related to the scope 16 and the optical adapter 2 mounted on the endoscope device 100, an ID number (individual identification information), and the like.

[Endoscope Calibration System 200]

Figure 4:
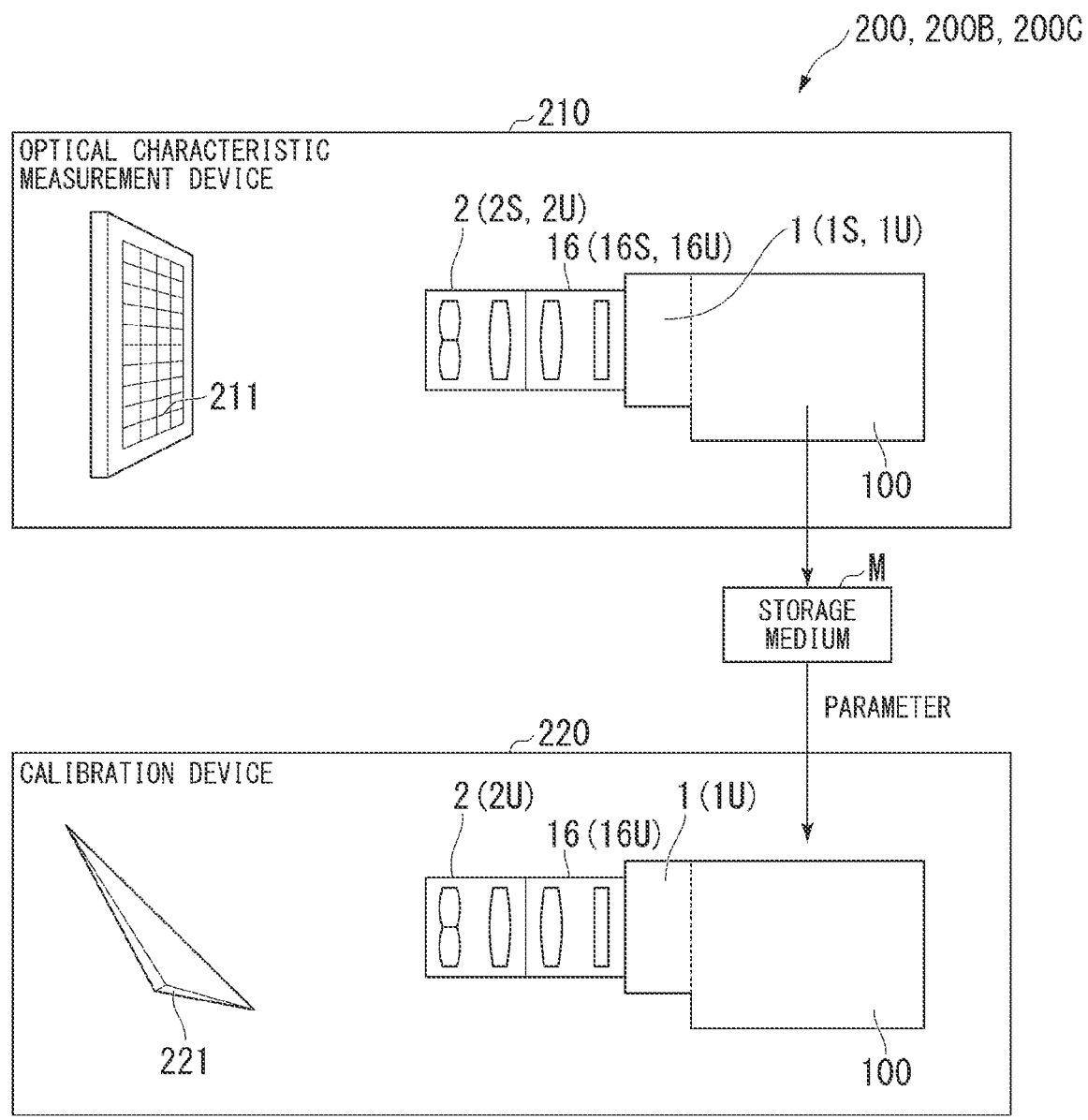
FIG. 4 is a diagram showing the endoscope calibration system.

FIG. 4 is a diagram showing an endoscope calibration system 200.

The endoscope calibration system 200 is a system for calibrating the optical system of the endoscope 1. The endoscope calibration system 200 includes an optical characteristic measurement device 210 and a calibration device 220.

[Optical Characteristic Measurement Device 210]

The optical characteristic measurement device 210 is a device for measuring optical characteristics including optical distortion peculiar to an optical system in which the scope 16 of the endoscope 1 and the optical adapter 2 are combined by using the endoscope device 100. The optical characteristic measurement device 210 is, for example, a jig device installed in the production factory of the endoscope device 100. The optical characteristic measurement device 210 includes an endoscope device 100 and a grid-shaped chart 211.

The optical characteristic measurement device 210 captures a grid-shaped chart 211 with the optical system of the endoscope 1 in which the optical adapter 2 and the scope 16 are combined, and measures a parameter indicating the optical characteristics of the optical system based on the acquired image. The measurement of the parameters based on the acquired image is performed by the main controller 32, the arithmetic processor 33, and the measurement processor 34 of the control device 3 of the endoscope device 100. The control device 3 of the endoscope device 100 is an example of a "parameter measuring part".

The optical characteristic measurement device 210 may further include an external arithmetic device that performs calculations in parameter measurement based on the acquired image. In this case, the external arithmetic device corresponds to the "parameter measuring part". The external arithmetic device is an arithmetic device separate from the control device 3, and is, for example, an external terminal or a server (including the cloud). The external terminal is, for example, a computer, a mobile phone, a tablet, a smartphone, or the like. The external terminal may be stored in the device main body 5. The external terminal or server (including the cloud) may perform a part of the processing performed by the control device 3.

The parameters indicating the optical characteristics of the optical system includes, for example, parameters such as the distance of the optical center of the optical system and the focal length, parameters related to the shape of the field mask, parameters for correcting the distortion of the optical system, and parameters for calculating three-dimensional coordinates from a two-dimensional image. The measurement of the parameters indicating the optical characteristics of the optical system is performed by a known method for measuring the optical characteristics described in Patent Document 1 (Japanese Unexamined Patent Application, First Publication No. 2007-171941) and the like.

The endoscope 1 for measuring the optical characteristics by the optical characteristic measurement device 210 is a reference endoscope 1S and a user endoscope 1U. The optical adapter 2 attached to the endoscope 1 for measuring optical characteristics is a reference optical adapter 2S and a user optical adapter 2U.

The reference endoscope 1S is an endoscope 1 selected as a reference for strain measurement in the production factory of the endoscope device 100. In the following description, the scope 16 of the reference endoscope 1S will be referred to as a "reference scope 16S (first scope)".

The user endoscope 1U is the endoscope 1 of the endoscope device 100 purchased by the user, and has the same optical specifications as the reference endoscope 15. In the following description, the scope 16 used by the user together with the user endoscope 1U used by the user will be referred to as "user scope 16U (second scope)". When the scope 16 is removable from the endoscope device 100, a plurality of types of user scopes 16U are attached to the user endoscope 1U. Even if the user scopes 16U are of the same type, the two different user scopes 16U have different optical characteristics due to individual differences.

The reference endoscope 1S and the user endoscope 1U have the same optical specifications but different endoscopes 1. Therefore, the reference scope 16S and the user scope 16U have individual differences in optical characteristics.

The reference optical adapter 2S (first optical adapter) is an optical adapter 2 selected as a reference for strain measurement in the production factory of the endoscope device 100.

The user optical adapter 2U (second optical adapter) is an optical adapter 2 purchased by the user. The user attaches the user optical adapter 2U to the user endoscope 1U, thereby using the user optical adapter 2U.

There are a plurality of types of the user scope 16U and the user optical adapter 2U corresponding to various observation applications and observation directions. Further, even if the user scope 16U and the user optical adapter 2U of the same type have individual differences in optical characteristics, each individual user scope 16U and user optical adapter 2U has unique optical characteristics. On the other hand, the reference scope 16S and the reference optical adapter 2S are not used by the user, but are one individual prepared for calibration in a production factory or the like.

[Calibration Device 220]

The calibration device 220 is a device that calibrates the optical system of the user endoscope 1U. The calibration device 220 is a device used by the user of the endoscope device 100. The calibration device 220 includes an endoscope device 100 used by the user and a measurement subject 221.

The calibration device 220 images the measurement subject 221, combines a plurality of parameters measured by the optical characteristic measurement device 210, and without actually performing the measurement in which the user optical adapter 2U and the user scope 16U are combined, estimates parameters for correcting the optical characteristics of the optical system of the user endoscope 1U in which the user optical adapter 2U and the user scope 16U are combined. Parameter estimation is performed by the main controller 32, the arithmetic processor 33, and the measurement processor 34 of the control device 3 of the endoscope device 100. The control device 3 of the endoscope device 100 is an example of a "parameter estimation part".

The calibration device 220 may further include an external arithmetic device that performs the arithmetic in the parameter estimation. In this case, the external arithmetic device corresponds to the "parameter estimation part". The external arithmetic device is an arithmetic device that is separate from the control device 3, and is, for example, an external terminal or a server (including the cloud). The external terminal is, for example, a computer, a mobile phone, a tablet, a smartphone, or the like. The external terminal may be stored in the device main body 5. The external terminal or server (including the cloud) may perform a part of the processing performed by the control device 3.

[Operation of Endoscope Calibration System 200]

Figure 5:
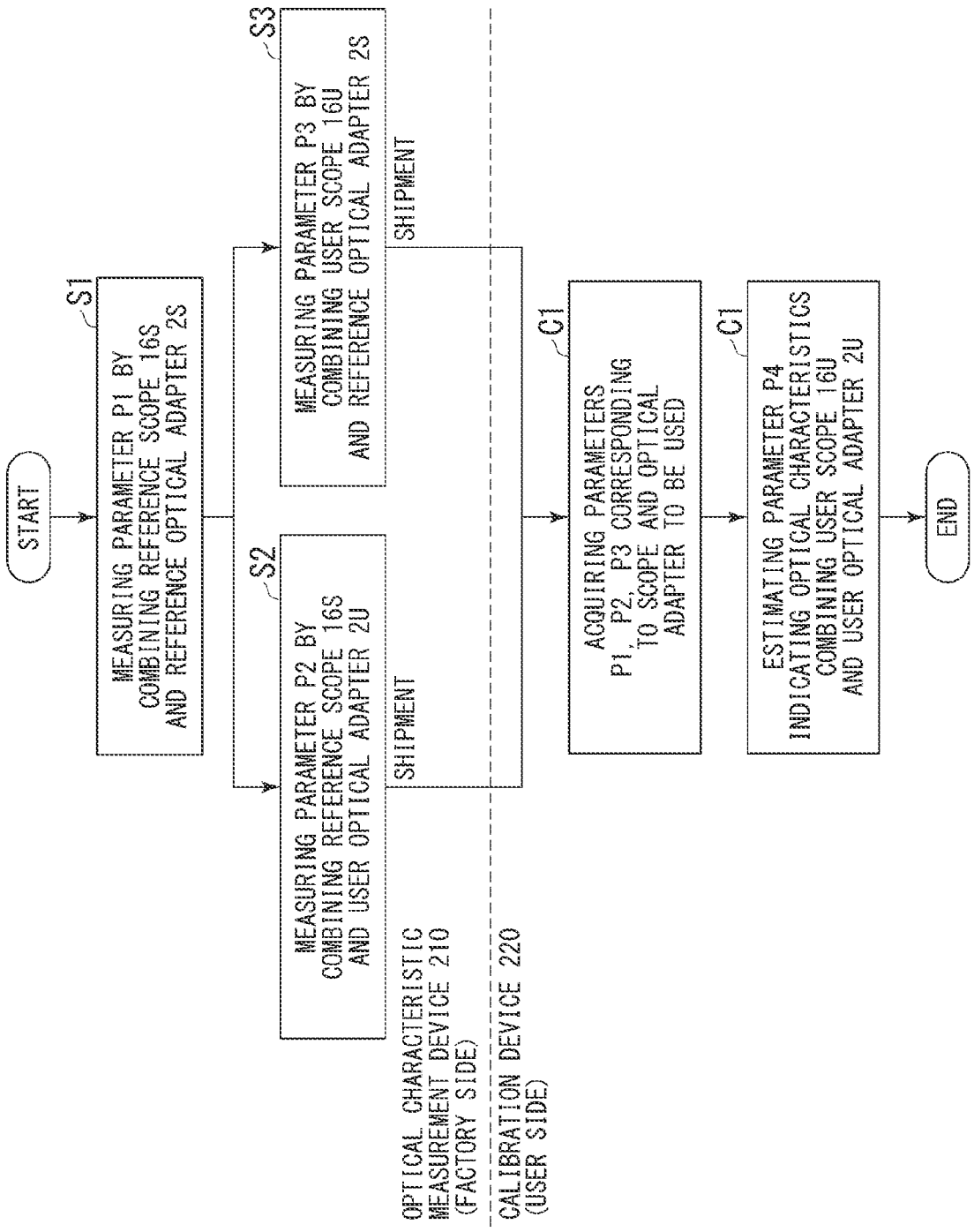
FIG. 5 is an operation flowchart of the endoscope calibration system.

Next, the operation of the endoscope calibration system 200 (calibration method of the endoscope device 100) will be described. FIG. 5 is an operation flowchart of the endoscope calibration system 200. First, the operation of parameter measurement by the optical characteristic measurement device 210 will be described. FIG. 6 is a diagram showing parameters measured by the optical characteristic measurement device 210.

<Step S1>

In preparation for step S1, the operator attaches the reference optical adapter 2S to the reference scope 16S mounted on the reference endoscope 1S, which is a production measurement jig. In step S1, the control device 3 (mainly, the main controller 32) of the endoscope device 100 measures a parameter P1 (first parameter) indicating the characteristics of the optical system in which the reference scope 16S of the reference endoscope 1S and the reference optical adapter 2S are combined. The control device 3 stores the parameter P1 in the recording medium M mounted on the endoscope device 100.

<Step S2>

In preparation for step S2, the operator attaches the user optical adapter 2U, which is one of the plurality of shipped user optical adapters 2U, to the reference scope 16S mounted on the reference endoscope 1S, which is a production measurement jig. In step S2, the control device 3 (mainly, the main controller 32) of the endoscope device 100 measures a parameter P2 (second parameter) indicating the characteristics of the optical system in which the reference scope 16S of the reference endoscope 1S and the user optical adapter 2U are combined. The control device 3 stores the parameter P2 in the recording medium M mounted on the endoscope device 100.

<Step S3>

In preparation for step S3, the operator attaches the reference optical adapter 2S, which is mounted on the user endoscope 1U and shipped, to the user scope 16U, which is one of the plurality of user optical adapters 2U. In step S3, the control device 3 (mainly, the main controller 32) of the endoscope device 100 measures a parameter P3 (third parameter) indicating the characteristics of an optical system in which the user scope 16U of the user endoscope 1U and the reference optical adapter 2S are combined. The control device 3 stores the parameter P3 in the scope internal storage 19 of the user scope 16U. Further, the control device 3 may store the parameter P1 measured in step S1 in the scope internal storage 19 of the user scope 16U. The parameter P3 may be stored in the recording medium M mounted on the endoscope device 100.

The order in which step S1, step S2, and step S3 are performed is not limited. For example, step S1 may be performed when the reference endoscope 1S including the reference scope 16S and the reference optical adapter 2S are selected. For example, step S2 may be performed when the user optical adapter 2U is shipped. Further, step S3 may be performed when the user endoscope 1U is shipped. Further, step S2 using the user optical adapter 2U may be performed after the individual user optical adapter 2U actually used by the user is identified. Step S3 using the user endoscope 1U may be performed after the individual of the user scope 16U actually used by the user is identified.

FIG. 7 is a diagram showing a storage destination of the measured parameters.

The recording medium M in which the parameter P1 and the parameter P2 are stored is shipped together with the user optical adapter 2U used for the measurement of the parameter P2.

Next, the operation of parameter estimation by the calibration device 220 will be described.

FIG. 8 is a diagram showing parameters estimated by the calibration device 220.

The calibration by the calibration device 220 is performed, for example, when the user newly purchased user optical adapter 2U is attached to the user endoscope 1U in use.

<Step C1>

In preparation for step C1, the operator attaches the user optical adapter 2U to the user scope 16U mounted on the user endoscope 1U. Further, the user attaches the recording medium M shipped together with the user optical adapter 2U to the endoscope device 100.

The control device 3 (mainly, the main controller 32) of the endoscope device 100 combines the parameter P1, the parameter P2, and the parameter P3 measured by the optical characteristic measurement device 210 in step C1, and estimates a parameter P4 (fourth parameter) that corrects the optical characteristics of the optical system of the user endoscope 1U in which the user optical adapter 2U and the user scope 16U are combined.

The control device 3 acquires the parameter P1 and the parameter P2 from the recording medium M via the storage medium reader 37. The control device 3 acquires the parameter P3 stored in the scope internal storage 19 of the user scope 16U.

The control device 3 of the endoscope device 100 reads the parameter P1 from the recording medium M and the scope internal storage 19 of the user scope 16U. The control device 3 of the endoscope device 100 may read the parameter P1 from either the recording medium M or the scope internal storage 19 of the user scope 16U. When the control device 3 reads the parameter P1 from both the recording medium M and the scope internal storage 19 of the user scope 16U, the control device 3 may perform a data consistency check of the parameter P1.

The control device 3 calculates the parameter P4 by subtracting the element of the parameter P1 from the result of adding the element of the parameter P2 and the element of the parameter P3. The order of addition and subtraction is not particularly limited. "Estimation" is to calculate the parameter P4 indicating the characteristics of the optical system of the user endoscope 1U in which the user scope 16U and the user optical adapter 2U, which are not actually measured, are combined, by using the parameters P1, P2, and P3. The control device 3 uses the estimated parameter P4 to correct the optical characteristics of the optical system of the user endoscope 1U in which the user optical adapter 2U and the user scope 16U are combined.

The control device 3 may image the measurement subject 221 with the optical system of the user endoscope 1U whose optical characteristics are corrected by the parameter P4, and confirm and fine-tune the optical system of the user endoscope 1U.

A plurality of types of parameters P1, parameters P2, and parameters P3 may be stored in the recording medium M. For example, since the parameters P2 and P3 are parameters measured using the user scope 16U or the user optical adapter 2U, it is desirable that a plurality of parameters P2 and P3 are stored according to the type or the number of individuals of the user scope 16U and the user optical adapter 2U. Further, a plurality of parameters P1, parameter P2 and parameter P3 may be stored in the storage 36 of the control device 3 or the scope internal storage 19 instead of the recording medium M.

Originally, it is desirable to acquire all the parameters indicating the optical characteristics of the optical system in which the user scope 16U of a plurality of types and individuals and the user optical adapter 2U of a plurality of types and individuals are combined. However, as described above, there are various types of the optical adapter 2 and the scope 16, and even the same type has different optical characteristics for each individual. That is, the number of combinations of the user scope 16U and the user optical adapter 2U is enormous, and it is impossible to actually measure the parameters corresponding to all the combinations in advance. In addition, the type and individual of the optical adapter 2 or scope 16 actually used by the user is unknown at the time of shipment, and it is difficult to predict in advance the combination that is likely to be used and measure the parameters. However, since there is only one reference scope 16S and reference optical adapter 2S, it is possible to acquire in advance parameters indicating the optical characteristics of the optical system of the endoscope 1 combined with the reference scope 16S or the reference optical adapter 2S. In view of such a problem, the present invention combines parameters P1, parameter P2, and parameter P3 that can be actually measured in advance, and regardless of the combination of scope and adapter used by the user, the parameter P4 can be estimated without actually performing the measurement in which the user scope 16U and the user optical adapter 2U are combined.

According to the endoscope calibration system 200 according to the present embodiment, by combining parameters indicating the optical characteristics of the optical system measured by the scope 16 to which the optical adapter 2 is attached, the inherent optical characteristics of the newly combined optical adapter 2 and scope 16 can be corrected. The optical characteristics of the endoscope 1 in which the optical adapter 2 and the scope 16 are combined can be corrected by a known method such as lattice chart imaging. However, when the scope 16 to which the optical adapter 2 is not attached is corrected, it is necessary that equipment and methods different from the correction when the optical adapter 2 is combined be used. Since it is not necessary to measure the parameters indicating the optical characteristics of the optical system of the scope 16 to which the optical adapter 2 is not attached, the equipment of the endoscope calibration system 200 can be simplified.

According to the endoscope calibration system 200 according to the present embodiment, without actually imaging the measurement subject 221, the correction of the optical characteristics of the optical system of the user endoscope 1U can be performed only by estimating the parameter P4. This makes it possible to easily correct the optical characteristics.

According to the endoscope calibration system 200 according to the present embodiment, the correction of the optical characteristics of the optical system of the user endoscope 1U in which the user optical adapter 2U and the user scope 16U can be performed only by adding or subtracting the parameters measured in advance. Therefore, the correction of the optical characteristics of the optical system of the user endoscope 1U can be performed at high speed without complicating the correction.

Although the first embodiment of the present invention has been described in detail with reference to the drawings, the specific configuration is not limited to this embodiment, and includes design changes and the like within a range that does not deviate from the gist of the present invention. In addition, the components shown in the above-described embodiments and modifications can be appropriately combined and configured.

(Modification 1-1)

In the above embodiment, a part of the parameter P1, the parameter P2, the parameter P3 and the parameter P4 indicating the measured optical characteristics is stored in the scope internal storage 19 of the user scope 16U. However, the storage destination of the parameters in the endoscope device 100 is not limited to the scope internal storage 19. The parameter storage destination in the endoscope device 100 may be the storage 36 of the control device 3.

(Modification 1-2)

In the above embodiment, the control device 3 performs the measurement of the parameter P1, the parameter P2, and the parameter P3, but the mode of the parameter measurement is not limited to this. For example, the above-mentioned external arithmetic device (particularly an external terminal) may calculate parameters P1, parameter P2, and parameter P3 based on the image acquired by the endoscope device 100.

Second Embodiment

The endoscope calibration system 200B according to the second embodiment of the present invention will be described with reference to FIGS. 9 to 10. In the following description, the same reference numerals will be given to the configurations common to those already described, and duplicate description will be omitted. The endoscope calibration system 200B is different from the endoscope calibration system 200 according to the first embodiment in that the optical characteristic measurement device 210 measures the parameter P4.

[Endoscope Calibration System 200B]

The endoscope calibration system 200B includes an optical characteristic measurement device 210 and a calibration device 220, similarly to the endoscope calibration system 200 according to the first embodiment.

[Operation of Endoscope Calibration System 200B]

Next, the operation of the endoscope calibration system 200B will be described. The optical characteristic measurement device 210 executes step S1, step S2, and step S3 as in the first embodiment.

When the user optical adapter 2U and the user endoscope 1U are a combination that can be used simultaneously in the production factory (for example, when the type and individual of the optical adapter 2 and scope 16 used by the user are known, such as when the user optical adapter 2U and the user endoscope 1U are a combination that can be used simultaneously in the production factory), the control device 3 (mainly, the main control unit 32) of the optical characteristic measurement device 210 further performs step S4.

<Step S4>

FIG. 9 is a diagram showing parameters measured by the optical characteristic measurement device 210.

In preparation for step S4, the operator attaches the user optical adapter 2U to the user scope 16U mounted on the user endoscope 1U. In step S4, the control device 3 (mainly, the main controller 32) of the endoscope device 100 actually measures the parameter P4 (fourth parameter) of the optical system of the user endoscope 1U in which the user scope 16U of the user endoscope 1U and the user optical adapter 2U are combined.

FIG. 10 is a diagram showing a storage destination of the measured parameters.

The control device 3 stores the actually measured parameter P4 in the scope internal storage 19 or the like of the user scope 16U.

The parameter P4 may be stored in the recording medium M or the like together with at least one of the parameter P1, the parameter P2, and the parameter P3. Further, since the parameter P4 is a parameter measured using the user scope 16U or the user optical adapter 2U, it is desirable that a plurality of parameters P4 are stored according to the type or the number of individuals of the user scope 16U or the user optical adapter 2U. However, considering the types and the number of individuals, the number of combinations that can be considered as the parameter P4 is enormous, so all that is required is to save the parameter P4 corresponding to the minimum combination that the user may actually use. Further, a plurality of parameters P4 may be stored not in the recording medium M but in the storage 36 of the main body of the device, the internal storage 19 of the scope, the storage in the external arithmetic device, and the like.

<Step D1>

Next, the calibration device 220 performs step D1. In step D1, the control device 3 (mainly, the main controller 32) of the endoscope device 100 determines whether or not the endoscope device 100 is an endoscope device in which the combination of the user optical adapter 2U and the user endoscope 1U is fixed, or whether the desired parameter P4 is stored. The control device 3 may receive information such as an individual identification number regarding the user optical adapter 2U and the user scope 16U, and perform the above determination. As the individual identification information, a method such as receiving from the scope internal storage 19 or the like at the time of connection, receiving from an external recording medium such as the recording medium M, or inputting known individual identification information by the operator can be considered. Further, the control device 3 may carry out the above determination by confirming that the parameter P4 is stored in the scope internal storage 19 or the storage 36 of the user scope 16U. The calibration device 220 then performs step D2.

<Step D2>

When the control device 3 determines that the endoscope device 100 is an endoscope device in which the combination of the user optical adapter 2U and the user endoscope 1U is fixed, the optical characteristics of the optical system of the endoscope 1U is corrected using the actually measured parameter P4. For example, when the parameter P4 using the information of the individual identification number (individual identification information) regarding the user optical adapter 2U and the user scope 16U is stored, the control device 3 uses the parameter P4 that is actually measured and stored.

When it is determined that the endoscope device 100 is not a fixed endoscope device in combination with the user optical adapter 2U and the user endoscope 1U, the control device 3 estimates the parameter P4 by the same method as in step C1 of the first embodiment, and corrects the optical characteristics of the optical system of the user endoscope 1U using the estimated parameter P4. For example, in a case where the parameter P4 using the individual identification number information (individual identification information) regarding the user optical adapter 2U and the user scope 16U is not stored, the control device 3 estimates the parameter P4.

According to the endoscope calibration system 200B according to the present embodiment, when the endoscope device 100 is a device in which the combination of the user optical adapter 2U and the user endoscope 1U is fixed, the optical characteristics of the optical system of the user endoscope 1U can be reliably corrected by using the actually measured highly reliable parameter P4 instead of the estimated parameter P4.

Although the second embodiment of the present invention has been described in detail with reference to the drawings, the specific configuration is not limited to this embodiment, and includes design changes and the like within a range that does not deviate from the gist of the present invention. In addition, the components shown in the above-described embodiments and modifications can be appropriately combined and configured.

Third Embodiment

The endoscope calibration system 200C according to the third embodiment of the present invention will be described with reference to FIG. 11. In the following description, the same reference numerals will be given to the configurations common to those already described, and duplicate description will be omitted. The endoscope calibration system 200C is different from the endoscope calibration system 200 according to the first embodiment in that the reference endoscope 1S is updated.
[Endoscope Calibration System 200C]
The endoscope calibration system 200C includes an optical characteristic measurement device 210 and a calibration device 220, similarly to the endoscope calibration system 200 according to the first embodiment.
[Operation of Endoscope Calibration System 200C]
Next, the operation of the endoscope calibration system 200B will be described. When the reference optical adapter 2S is updated to a new optical adapter 2 (hereinafter referred to as "second reference optical adapter 2T") after step S1, step S2, step S3 and step C1 of the first embodiment, the control device 3 of the optical characteristic measurement device 210 further performs steps R1 and R2.
<Step R1>
FIG. 11 is a diagram showing parameters measured by the optical characteristic measurement device 210.

In preparation for step R1, the operator attaches the second reference optical adapter 2T to the reference scope 16S mounted on the reference endoscope 1S. In step R1, the control device 3 (mainly, the main controller 32) of the endoscope device 100 measures the update parameter P1' (update first parameter) of the optical system in which the reference scope 16S of the user endoscope 1U and the second reference optical adapter 2T are combined.

<Step R2>
In preparation for step R2, the operator attaches the second reference optical adapter 2T to the user scope 16U mounted on the user endoscope 1U. In step R2, the control device 3 (mainly, the main controller 32) of the endoscope device 100 measures the update parameter P3' (update third parameter) of the optical system in which the user scope 16U of the user endoscope 1U and the second reference optical adapter 2T are combined.

The order in which steps R1 and R2 are performed is not limited. For example, step R1 may be performed when the reference scope 16S is updated. For example, step R2 may be performed when the user endoscope 1U is shipped.

The control device 3 stores the update parameter P1' and the update parameter P3' in the scope internal storage 19 of the user scope 16U.

Next, the calibration device 220 performs step C1 in the same manner as in the first embodiment. In step C1, the control device 3 (mainly, the main controller 32) of the endoscope device 100 estimates the update parameter P4' using the update parameter P1' instead of the parameter P1 and using the update parameter P3' instead of the parameter P3.

According to the endoscope calibration system 200C according to the present embodiment, even when the reference optical adapter 2S is updated, the optical characteristics of the optical system of the user endoscope 1U can be corrected by measuring the parameters again.

The update parameter P1' and the update parameter P3' are stored in the recording medium M or the scope internal storage 19. It is possible to determine that the same standard equipment is used, by collating the parameters P1 and P3, which are recorded in the recording medium M and the internal storage 19 of the scope, with the update parameter P1' and the update parameter P3', by the control device 3 or the like. As a result, it is possible to confirm that the measurement is always performed with the latest calibration equipment, and the reliability of the measurement result can be ensured.

Although the third embodiment of the present invention has been described in detail with reference to the drawings, the specific configuration is not limited to this embodiment, and includes design changes and the like within a range that does not deviate from the gist of the present invention. In addition, the components shown in the above-described embodiments and modifications can be appropriately combined and configured.
(Modification 3-1)
In the above embodiment, the device to be updated is the reference optical adapter 2S. However, even when the reference scope 16S is updated, the optical characteristics of the optical system of the user endoscope 1U can be corrected by the same method. In this case, the parameter P2 becomes the update parameter P2' for which the optical characteristics are measured by combining the user optical adapter 2U and the update user scope 16T, and is stored in the recording medium M or the scope internal storage 19.

Fourth Embodiment

The Endoscope Calibration System 200D According to the Fourth Embodiment of the present invention will be described with reference to FIG. 12. In the following description, the same reference numerals will be given to the configurations common to those already described, and duplicate description will be omitted. The endoscope calibration system 200D is different from the endoscope calibration system 200 and the like according to the above embodiment in that the server 300 is further provided as an external arithmetic device.

[Endoscope Calibration System 200D]

Figure 12:
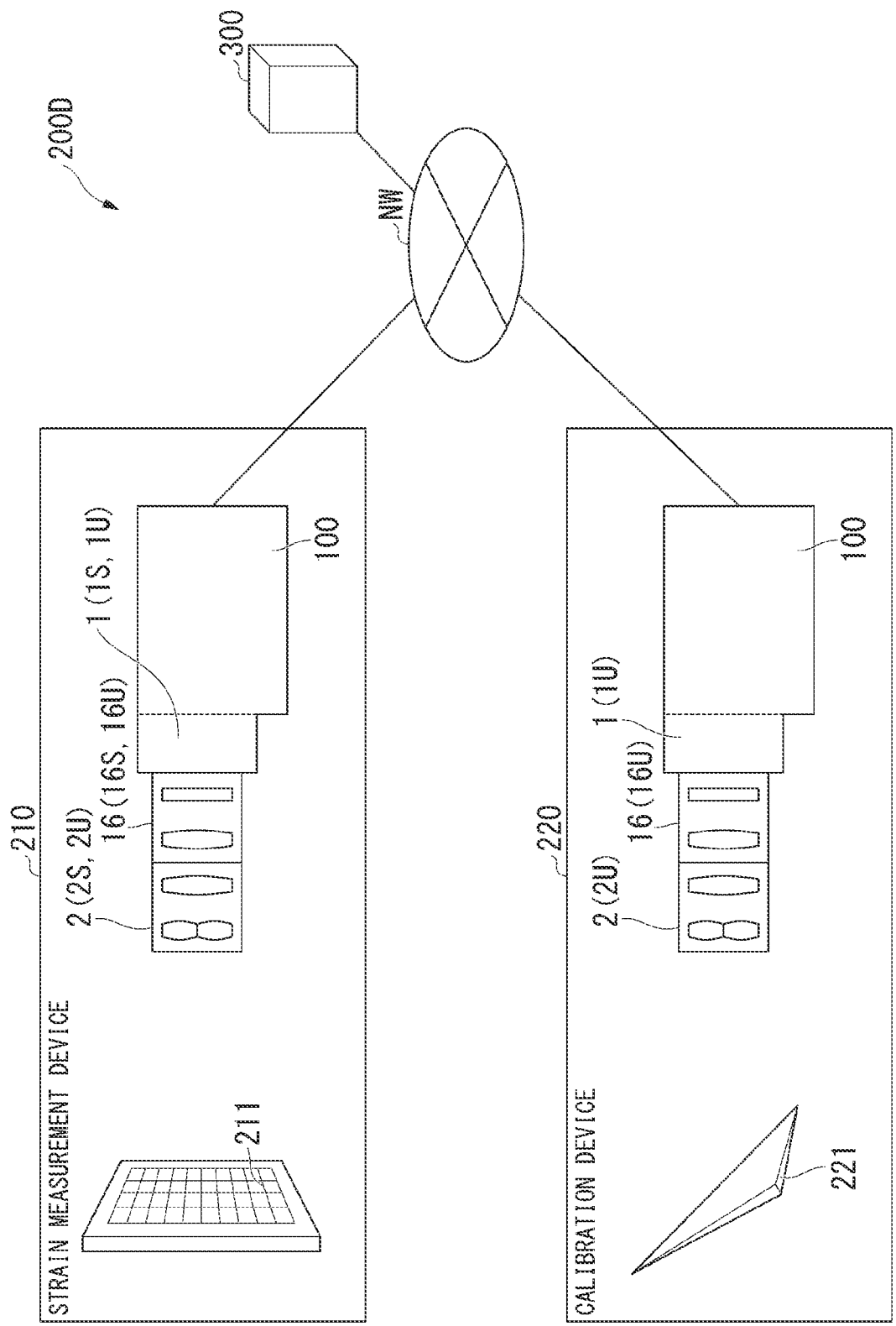
FIG. 12 is a diagram showing an endoscope calibration system according to a fourth embodiment.

FIG. 12 is a diagram showing an endoscope calibration system 200D.

The endoscope calibration system 200D is a system for calibrating the optical system of the endoscope 1. The endoscope calibration system 200D includes an optical characteristic measurement device 210, a calibration device 220, and a server 300. The optical characteristic measurement device 210, the calibration device 220, and the server 300 are connected via the network NW. In this case, the optical characteristic measurement device 210 and the calibration device 220 include a communication device that communicates with the server 300 through the network NW. Further, the control device 3 of the endoscope device 100 may include a communication device.

The network NW may be a wide area network (WAN) such as the so-called Internet, may be a private network (LAN) in a building provided with an optical characteristic measurement device 210 and a calibration device 220, or may be a combination thereof. Further, the network NW may be either wired communication or wireless communication. Other devices such as access points may intervene in the communication between the devices.

The server 300 is a device that relays data, stores data, calculates data, executes a program, and the like. In the endoscope calibration system 200D, some or all of the parameters measured by the optical characteristic measurement device 210 are stored in the server 300. The types of parameters stored in the server 300 are not limited. The server 300 may be provided separately from the endoscope device 100, or may be placed in a cloud environment. Further, the server 300 may play the role of the scope internal storage 19 and the storage 36.

The calibration device 220 acquires and uses the parameters measured by the optical characteristic measurement device 210 not from the recording medium M or the like but from the server 300 via the network NW.

According to the endoscope calibration system 200D according to the present embodiment, the optical characteristics of the optical system of the user endoscope 1U can be corrected by using the parameters acquired not from the recording medium M or the like but via the network NW. As a result, the operator or the user can remotely receive various parameters and correct the optical characteristics of the optical system of the endoscope 1 without carrying and inserting the recording medium M or the like. In particular, in a case where the user introduces a new user scope 16U or user optical adapter 2U, when the parameters P2 and P3 related to them are stored in the server 300, the parameter P4 can be calculated immediately and the calibration can be performed quickly.

Although the fourth embodiment of the present invention has been described in detail with reference to the drawings, the specific configuration is not limited to this embodiment, and includes design changes and the like within a range that does not deviate from the gist of the present invention. In addition, the components shown in the above-described embodiments and modifications can be appropriately combined and configured.

(Modification 4-1)

In the above embodiment, the server 300 stores the parameters measured by the optical characteristic measurement device 210. However, the aspect of the server 300 is not limited to this. The server 300 may perform the calculation estimated by the parameter P4 and have the calibration device 220 acquire the parameter P4. In this case, the server 300 corresponds to the "parameter estimation part".

The "parameter measurement part" and "parameter estimation part" illustrated in each embodiment are any combination of the control device 3 of the endoscope device 100, the external arithmetic device (including the external terminal), the server 300, and the like.

The program in each embodiment may be recorded on a computer-readable recording medium, and the program recorded on the recording medium may be read by a computer system and executed. The "computer system" includes hardware such as an OS and peripheral devices. Further, the "computer-readable recording medium" refers to a portable medium such as a flexible disk, a magneto-optical disk, a ROM, or a CD-ROM, or a storage device such as a hard disk built in a computer system. Further, a "computer-readable recording medium" may include those that dynamically hold programs for a short period of time like a communication line when a program is transmitted via a network such as the Internet or a communication line such as a telephone line, and those that hold the program for a certain period of time like the volatile memory inside a computer system that serves as a server or client in that case. Further, the above-mentioned program may be a program for realizing a part of the above-mentioned functions, and may be a program for realizing the above-mentioned functions in combination with a program already recorded in the computer system.

What is claimed is:

1. An endoscopic calibration system for calibrating an endoscope comprising a fourth optical system in which a second scope and a second optical adapter are combined, the endoscope calibration system comprising:
   one or more processors comprising hardware, the one or more processors being configured to:
      acquire a first parameter indicating optical characteristics of a first optical system in which a first scope and a first optical adapter are combined;
      acquire a second parameter indicating optical characteristics of a second optical system in which the first scope and the second optical adapter are combined;
      acquire a third parameter indicating optical characteristics of a third optical system in which the second scope and the first optical adapter are combined;
      access a storage storing a preexisting fourth parameter for correcting optical characteristics of the fourth optical system in which the second scope and the second optical adapter are combined;
      determine whether to use the preexisting fourth parameter stored in the storage to correct the optical characteristics of the fourth optical system;
      in response to determining to use the preexisting fourth parameter stored in the storage, correct the optical characteristics of the fourth optical system using the preexisting fourth parameter stored in the storage;
      in response to determining not to use the preexisting fourth parameter stored in the storage, estimate a new fourth parameter for correcting the optical characteristics of the fourth optical system using the first parameter, the second parameter, and the third parameter; and
      correct the optical characteristics of the fourth optical system using the new fourth parameter estimated.

2. The endoscope calibration system according to claim 1, wherein in estimating the new fourth parameter, the one or more processors are configured to estimate a correcting parameter for correcting an optical system distortion of the fourth optical system.

3. The endoscope calibration system according to claim 2, wherein in estimating the new fourth parameter, the one or more processors are configured to estimate a mask-shape parameter relating to a field mask shape of the fourth optical system.

4. The endoscope calibration system according to claim 1, wherein the first parameter, the second parameter, and the third parameter are parameters measured by a same method for measuring optical characteristics.

5. The endoscope calibration system according to claim 1, wherein the first parameter, the second parameter, and the third parameter are measured from corresponding images captured with the corresponding one of the first optical system, the second optical system, and the third optical system.

6. The endoscope calibration system according to claim 1, wherein the one or more processors are configured to acquire the second parameter from the storage, and wherein the storage is mounted on the endoscope.

7. The endoscope calibration system according to claim 1, wherein the one or more processors are configured to acquire the third parameter from the storage, the storage being provided in the endoscope, or another storage provided in the second scope.

8. The endoscope calibration system according to claim 1, wherein the one or more processors are configured to acquire at least a part of the first parameter, the second parameter, and the third parameter from a server.

9. The endoscope calibration system according to claim 1, wherein the one or more processors are configured to estimate the new fourth parameter by adding or subtracting the first parameter, the second parameter, and the third parameter.

10. The endoscope calibration system according to claim 1, wherein the one or more processors are provided in the endoscope.

11. The endoscope calibration system according to claim 1, wherein the one or more processors are configured to communicate with the endoscope comprising the fourth optical system.

12. An endoscope device comprising:
an endoscope comprising a fourth optical system in which a second scope and a second optical adapter are combined; and
one or more processors comprising hardware, wherein the one or more processors are configured to:
acquire;
a first parameter indicating optical characteristics of a first optical system in which a first scope and a first optical adapter are combined;
a second parameter indicating optical characteristics of a second optical system in which the first scope and the second optical adapter are combined; and
a third parameter indicating optical characteristics of a third optical system in which the second scope and the first optical adapter are combined;
access a storage storing a preexisting fourth parameter for correcting optical characteristics of the fourth optical system in which the second scope and the second optical adapter are combined;
determine whether to use the preexisting fourth parameter stored in the storage to correct the optical characteristics of the fourth optical system;
in response to determining to use the preexisting fourth parameter stored in the storage, correct the optical characteristics of the fourth optical system using the preexisting fourth parameter stored in the storage;
in response to determining not to use the preexisting fourth parameter stored in the storage, estimate a new fourth parameter for correction the optical characteristics of the fourth optical system using the first parameter, the second parameter, and the third parameter; and
correct the optical characteristics of the fourth optical system using the new fourth parameter estimated.

13. A method for calibrating an endoscope comprising a fourth optical system in which a second scope and a second optical adapter are combined, comprising:
acquiring a first parameter indicating optical characteristics of a first optical system in which a first scope and a first optical adapter are combined;
acquiring a second parameter indicating optical characteristics of a second optical system in which the first scope and the second optical adapter are combined;
acquiring a third parameter indicating optical characteristics of a third optical system in which a second scope and the first optical adapter are combined;
accessing a storage storing a preexisting fourth parameter for correcting optical characteristics of the fourth optical system in which the second scope and the second optical adapter are combined;
determining whether to use the preexisting fourth parameter stored in the storage to correct the optical characteristics of the fourth optical system;
in response to determining to use the preexisting fourth parameter stored in the storage, correcting the optical characteristics of the fourth optical system using the preexisting fourth parameter stored in the storage;
in response to determining not to use the preexisting fourth parameter stored in the storage, estimating a new fourth parameter for correcting the optical characteristics of the fourth optical system using the first parameter, the second parameter, and the third parameter; and
correcting the optical characteristics of the fourth optical system using the new fourth parameter estimated.

14. A non-transitory computer-readable storage medium storing an endoscope calibration program for calibrating an endoscope comprising a fourth optical system in which a second scope and a second optical adapter are combined, wherein the endoscope calibration program causes a computer to at least execute:
acquiring a first parameter indicating optical characteristics of a first optical system in which a first scope and a first optical adapter are combined;
acquiring a second parameter indicating optical characteristics of a second optical system in which the first scope and the second optical adapter are combined;
acquiring a third parameter indicating optical characteristics of a third optical system in which a second scope and the first optical adapter are combined;
accessing a storage storing a preexisting fourth parameter for correcting optical characteristics of the fourth optical system in which the second scope and the second optical adapter are combined;
determining whether to use the preexisting fourth parameter stored in the storage to correct the optical characteristics of the fourth optical system;
in response to determining to use the preexisting fourth parameter stored in the storage, correcting the optical characteristics of the fourth optical system using the preexisting fourth parameter stored in the storage;

in response to determining not to use the preexisting fourth parameter stored in the storage, estimating a new fourth parameter for correcting the optical characteristics of the fourth optical system using the first parameter, the second parameter, and the third parameter; and correcting the optical characteristics of the fourth optical system using the new fourth parameter estimated.

* * * * *